United States Patent [19]

Negrelli et al.

[11] Patent Number: 4,989,229
[45] Date of Patent: Jan. 29, 1991

[54] COUNTERBALANCE ASSEMBLY FOR DIAGNOSTIC IMAGING EQUIPMENT

[75] Inventors: Donald E. Negrelli, Gates Mills; Donald E. Kolbfleisch, Burton; Anthony D. Szpak, Parma, all of Ohio

[73] Assignee: Picker International, Inc., Highland Heights, Ohio

[21] Appl. No.: 441,041

[22] Filed: Nov. 22, 1989

[51] Int. Cl.⁵ .............. H05G 1/02; H05G 1/06; F16L 3/00; E04G 3/00
[52] U.S. Cl. .................. 378/198; 378/197; 378/193; 378/196; 248/123.1; 248/292.1; 248/297.1; 248/280.1
[58] Field of Search ............ 378/196, 197, 198, 194, 378/193, 168, 284, 124, 195; 248/123.1, 292.1, 297.1, 280.1, 281.1, 364, 325, 324; 212/260, 196; 250/363.05, 363.08; 403/350, 351, 111, 112

[56] References Cited

U.S. PATENT DOCUMENTS

| 3,770,955 | 11/1973 | Tomita et al. | 378/197 |
| 3,870,886 | 3/1975 | Casale | 250/363.08 |
| 4,695,024 | 9/1987 | Haven | 248/281.1 |
| 4,768,744 | 9/1988 | Leeds et al. | 248/280.1 |
| 4,770,384 | 9/1988 | Kuwazima et al. | 248/280.1 |

Primary Examiner—Janice A. Howell
Assistant Examiner—Don Wong
Attorney, Agent, or Firm—Fay, Sharpe, Beall, Fagan, Minnich & McKee

[57] ABSTRACT

A counterbalance assembly (A) provides support for diagnostic imaging equipment such as an x-ray source (B). A fluid spring (F) is utilized to counteract the weight of the source and provide controlled movement of the source. A one-way clutch (100) cooperates with an arm assembly (E) that interconnects a source mounting member (D) with a base member (C) to limit movement of the arm and source. A locking assembly (112) is associated with the clutch to selectively actuate and deactuate the clutch.

23 Claims, 7 Drawing Sheets

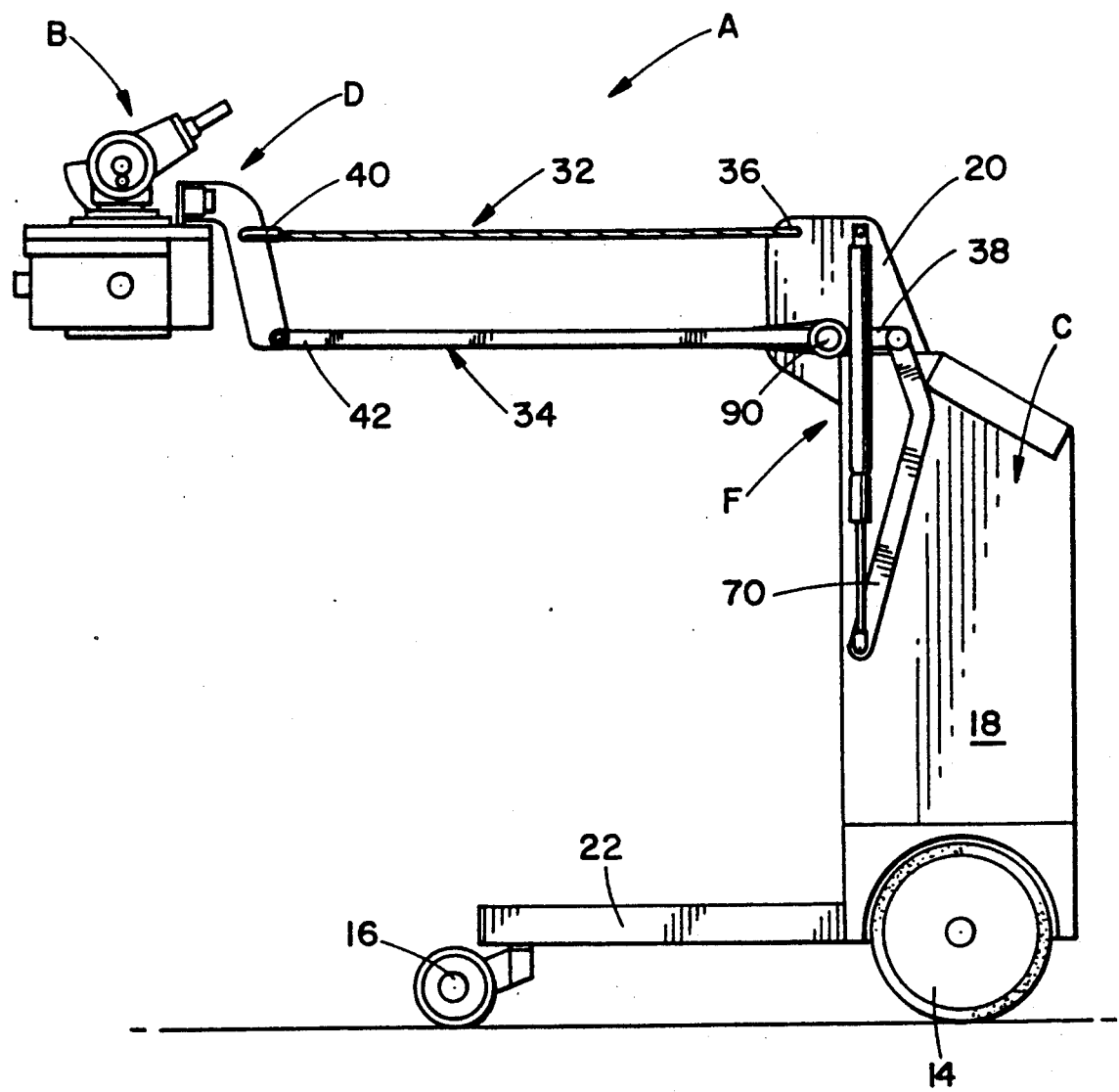
FIG. IB

COUNTERBALANCE ASSEMBLY FOR DIAGNOSTIC IMAGING EQUIPMENT

BACKGROUND OF THE INVENTION

The present invention relates to the art of diagnostic equipment. It finds particular application in conjunction with a mobile x-ray unit and will be described with particular reference thereto. However, it is appreciated that the present invention may also be applicable to other environments in which support of diagnostic equipment is required.

Diagnostic equipment such as x-ray sources are typically mounted on a boom or movable arm to allow selective positioning of the source relative to a patient. The x-ray source is attached at one end of the arm and because of the weight of the source, the arm is usually biased to support the x-ray source.

Conventional x-ray units employ mechanical springs such as coil or helical springs to bias the arm in a direction opposite from the force or load imposed on the arm by the x-ray source. The spring is designed to counteract all or substantially all of the weight of the source, depending on the design of the support equipment. These counterbalance assemblies require a large mechanical spring to counteract the weight of the x-ray source and permit an operator to easily position the source as needed. Additionally, these mechanical spring arrangements generally have a small energy to unit weight ratio necessitating a large spring that results in a correspondingly large structure.

Still other drawbacks are associated with the use of springs of this type as counterbalance assemblies. Oftentimes, the x-ray source is designed for selective removal from the end of the arm. Care must be used to assure that the arm is stabilized and secured while the source is removed. Otherwise, the biasing force of the mechanical spring is unrestrained once the weight of the source, that normally opposes the biasing force, is removed.

Another problem associated with the use of mechanical springs as the biasing arrangement in prior devices is the lack of controlled movement. Usually, the spring counteracts or supports the dead weight of the source so that even small forces provide relative ease of movement. At first glance, this may not appear to be a problem. Unfortunately, the problem is magnified if the spring fails and no counteractive force is imposed on the arm to balance the weight of the x-ray source. The source or anything disposed in the path of the source could be subjected to damage from such uncontrolled movement.

In accordance with the present invention, a new and improved counterbalance assembly is provided to support the diagnostic equipment. The new and improved counterbalance assembly also provides for controlled movement of the x-ray unit, even if the biasing arrangement fails.

SUMMARY OF THE INVENTION

In accordance with the present invention, a counterbalance assembly for supporting diagnostic imaging equipment is provided which includes an arm pivotally secured at opposite ends to a base member and a mounting member. The diagnostic equipment is received on one end of the arm and a fluid biasing means is associated with the arm to counteract the weight of the diagnostic equipment.

In accordance with another aspect of the invention, a clutch selectively controls movement between the mounting member and the base member.

In accordance with yet another aspect of the invention, the clutch may be selectively actuated and deactuated by a locking assembly.

In accordance with still another aspect of the invention, the arm includes a bent linking member for interconnection with the fluid biasing means. An eccentric cam can alternatively be used for adjusting the amount of biasing force as the arm is moved.

One advantage of the present invention is that the diagnostic equipment is effectively counterbalanced.

Another advantage of the present invention is the ability to provide selective one-way movement of the source.

Another advantage of the present invention is that the biasing force is automatically adjusted in response to movement of the arm.

Another advantage of the present invention is that the x-ray source is more likely to move in a slow, controlled fashion, particularly if the biasing arrangement fails.

Still further advantages of the present invention will become apparent to those of ordinary skill in the art upon reading and understanding the following detailed description of the preferred embodiments.

BRIEF DESCRIPTION OF THE DRAWINGS

The invention may take form in various components or arrangements of components. The drawings are only for purposes of illustrating the preferred embodiments and are not to be construed as limiting the invention.

FIG. 1B is an elevational view of the counterbalance showing the x-ray source in an intermediate position;

FIG. 9 is an alternative fluid biasing arrangement for controlling the velocity of the source and arm;

FIG. 10 is an elevational view of a "dead man" release and locking arrangement.

DETAILED DESCRIPTION OF THE PREFERRED EMBODIMENTS

Figure 1A:
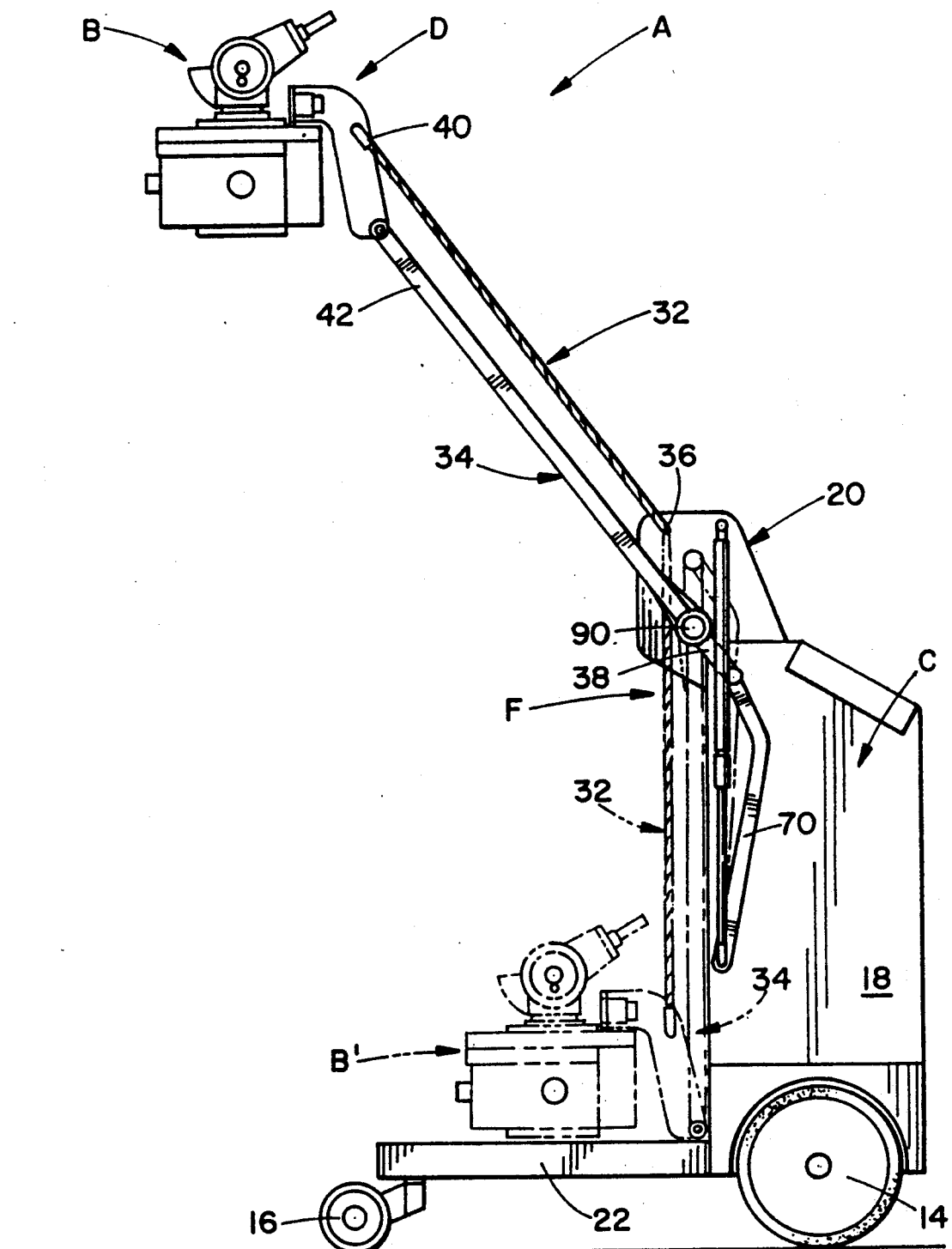
FIG. 1A is an elevational view of the counterbalance assembly showing an x-ray source in a raised position and a lower storage position is shown in phantom.
Figure 2:
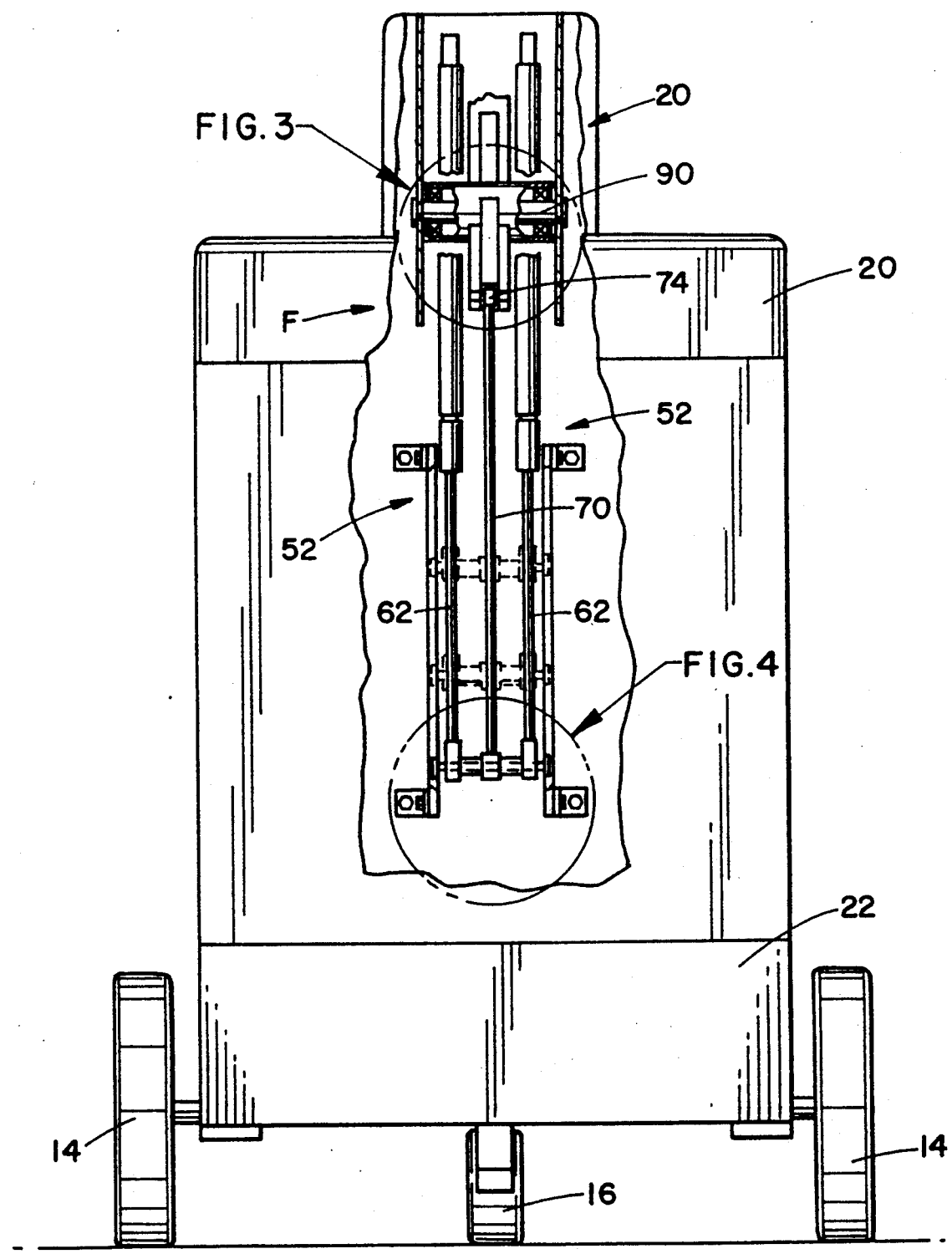
FIG. 2 is an elevational view taken from the right hand side of FIG. 1 with selected portions cut away to more particularly illustrate the internal components.

With reference to FIGS. 1 and 2, a counterbalance and support assembly A for supporting a non-invasive examination means such as an x-ray source B includes a base member C, a mounting member D interconnected through an arm assembly E to the base member, and a fluid biasing means F. The camera is shown in three different locations to represent movement relative to the base member C.

In the preferred arrangement, the base member is a portable or mobile unit having enlarged rear wheels 14 and a smaller, castered front wheel 16. An enlarged rear portion 18 of the base member includes a pivot region 20. A forwardly extending platform 22 extends from the base of rear portion 18 and receives the x-ray source in a secure, guarded position, hereinafter referred to as the storage position, when it is desired to move the support assembly to a different location. Of course the particular structural arrangement of the base member is merely one of a number of structures that facilitate transport and secure mounting of the x-ray source as will be apparent to one of ordinary skill in the art. Still other base member arrangements may be utilized without departing from the scope and intent of the subject invention.

The arm assembly E is particularly defined by first and second arms 32, 34 extending between the pivot region 20 of the base member and the x-ray source B. Preferably, each of the arms 32, 34 has a first end 36, 38, respectively, pivotally secured to region 20 of the base member. Likewise, second ends 40, 42, of the arms 32, 34, respectively, are pivotally secured to the mounting member D as will become more apparent below. This arrangement provides what is conventionally known as a four bar linkage between the base member and mounting member. Such a four bar linkage utilizes the parallel arrangement of the first and second arms 32, 34 to provide a stable, swinging movement between the mounting member and base member. The mounting member, as well as the source secured thereto, maintains the same orientation in the plane defined by the first and second arms, even though the particular position of the mounting member within that plane may vary. In other words, the base member and mounting member are always disposed in parallel relation, even though the distance between these members may vary.

Figure 3:
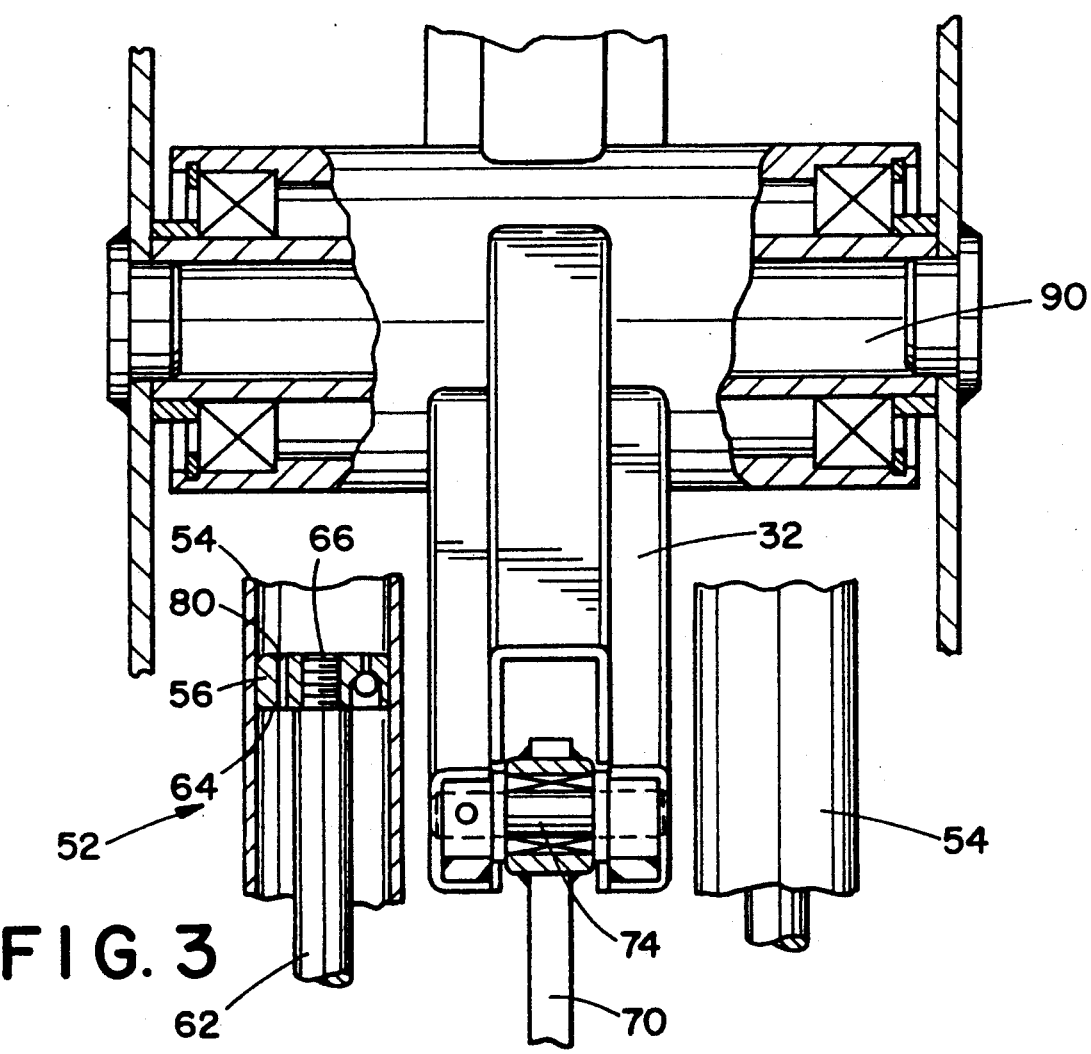
FIG. 3 is an enlarged detailed view of the upper, encircled area in FIG. 2.
Figure 4:
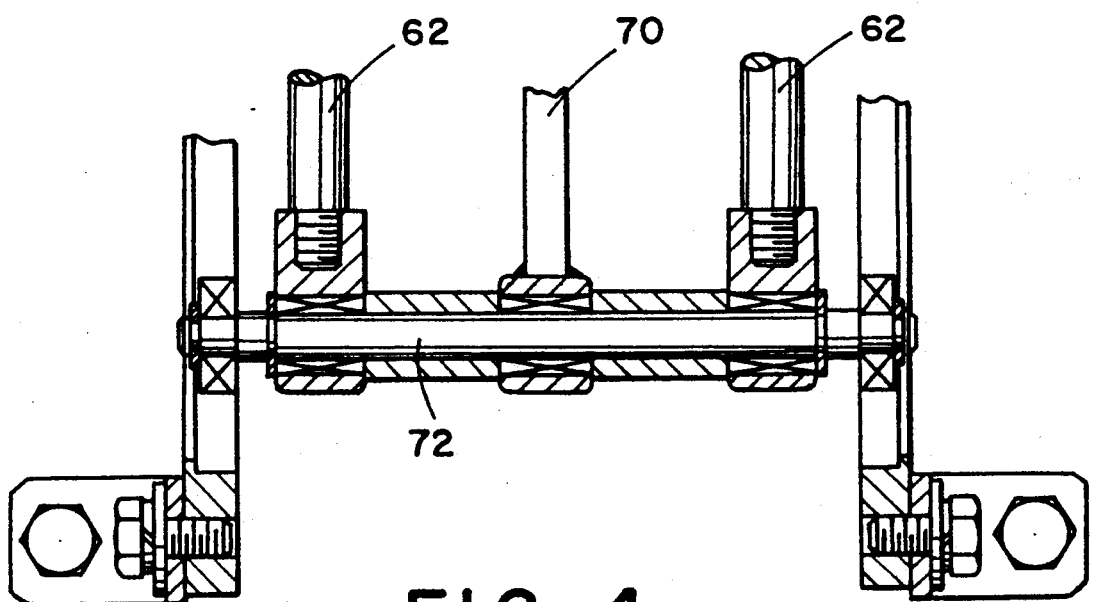
FIG. 4 is an enlarged detailed view of the lower, encircled area in FIG. 2.

With continued reference to FIGS. 1 and 2, and additional reference to FIGS. 3 and 4, the fluid biasing means F is defined by gas cylinder assembly 52. The gas cylinder assembly effectively supports the weight of both the x-ray source B, mounting member D, and arms 32, 34. The cylinder assembly preferably includes one or more cylinders 54, preferably two cylinders. Since construction of one of the cylinders is identical to the other, description of one of the cylinders is applicable to the other unless particularly noted otherwise. The cylinder 54 receives a piston 56 dividing the cylinder into first and second chambers 58, 60. As the piston reciprocates, one chamber will increase in size while the other chamber correspondingly decreases in size.

A rod 62 extends outwardly from the cylinder 54 and has one end secured to a first or lower face 64 of the piston. The other end of the rod is secured to a bent link arm 70, or pair of link arms, by means of a pin 72. The link arm, in turn, is connected by pin 74 at its other end to the arm 34.

A restricted orifice or passage so is defined through the piston to establish fluid communication between the first and second chambers. Since the rod 62 extends from the lower face of the piston, the fluid pressure in chambers 58 and 60, although equal, acts on different areas. That is, a much larger surface area is defined on the upper face 66 of the piston than on the lower face 64. Thus, even if there is an equal pressure of, for example, 2,000 psi on either side of the piston, the piston and rod will be urged downwardly since a larger force is imposed on the upper face of the piston. Through selective control of the difference in area between the upper and lower faces of the piston, as well as the amount of pressure in the cylinder, force on the piston and rod can be carefully controlled.

If no upward force is conveyed through the rod to the piston, the piston will always migrate to the lower end of the cylinder, i.e., fully extending the rod. As illustrated in FIG. 1, full extension of the rod rotates the arm 34 about pin 90 through the link arm 70. Thus, the weight of the x-ray source and the torque arm defined from the first end 42 to pin 90 is less than the moment or torque imposed by the biasing force of the gas cylinder assembly through the link arm and the first end 384 of the arm. In fact, the assembly is preferably designed so that the arm 34 and x-ray source are always urged to a first or upper location as shown by the solid line in FIG. 1. This corresponds to full extension of the rod.

If an operator desires to move the x-ray unit to an intermediate location, an additional downward force is manually applied to the source by an operator, which increases the counter-clockwise moment around pin 90. This moment will overcome the moment resulting from the biasing force of the gas cylinder and the arms 32, 34 will rotate toward an intermediate position as illustrated in phantom at B' in FIG. 1. In fact, if desired, the entire source can be urged to the storage position where it is disposed over the platform 22, also illustrated in phantom at B" in FIG. 1.

Figure 5:
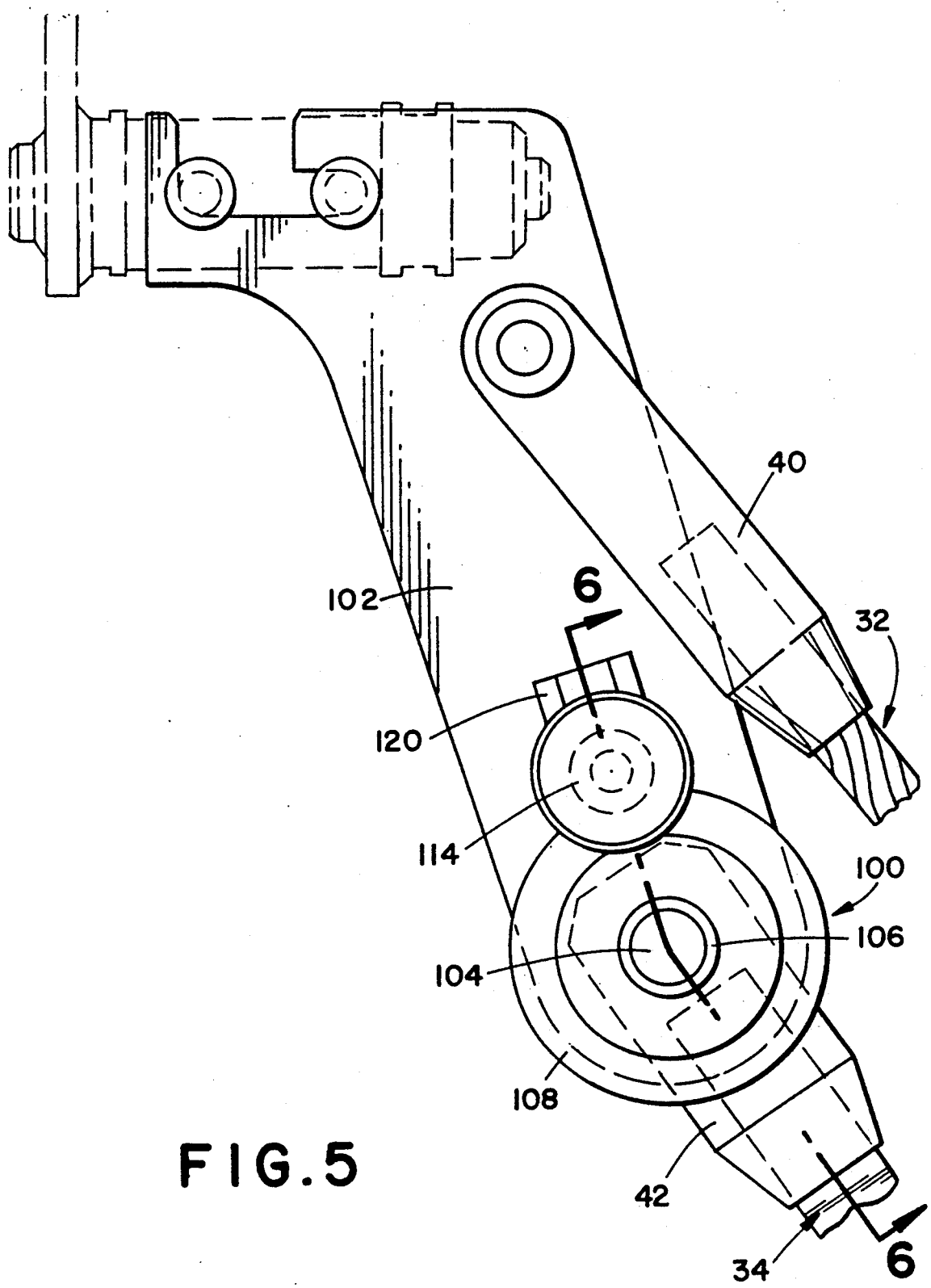
FIG. 5 is an enlarged elevational view of the arm and mounting member interconnection.
Figure 6:
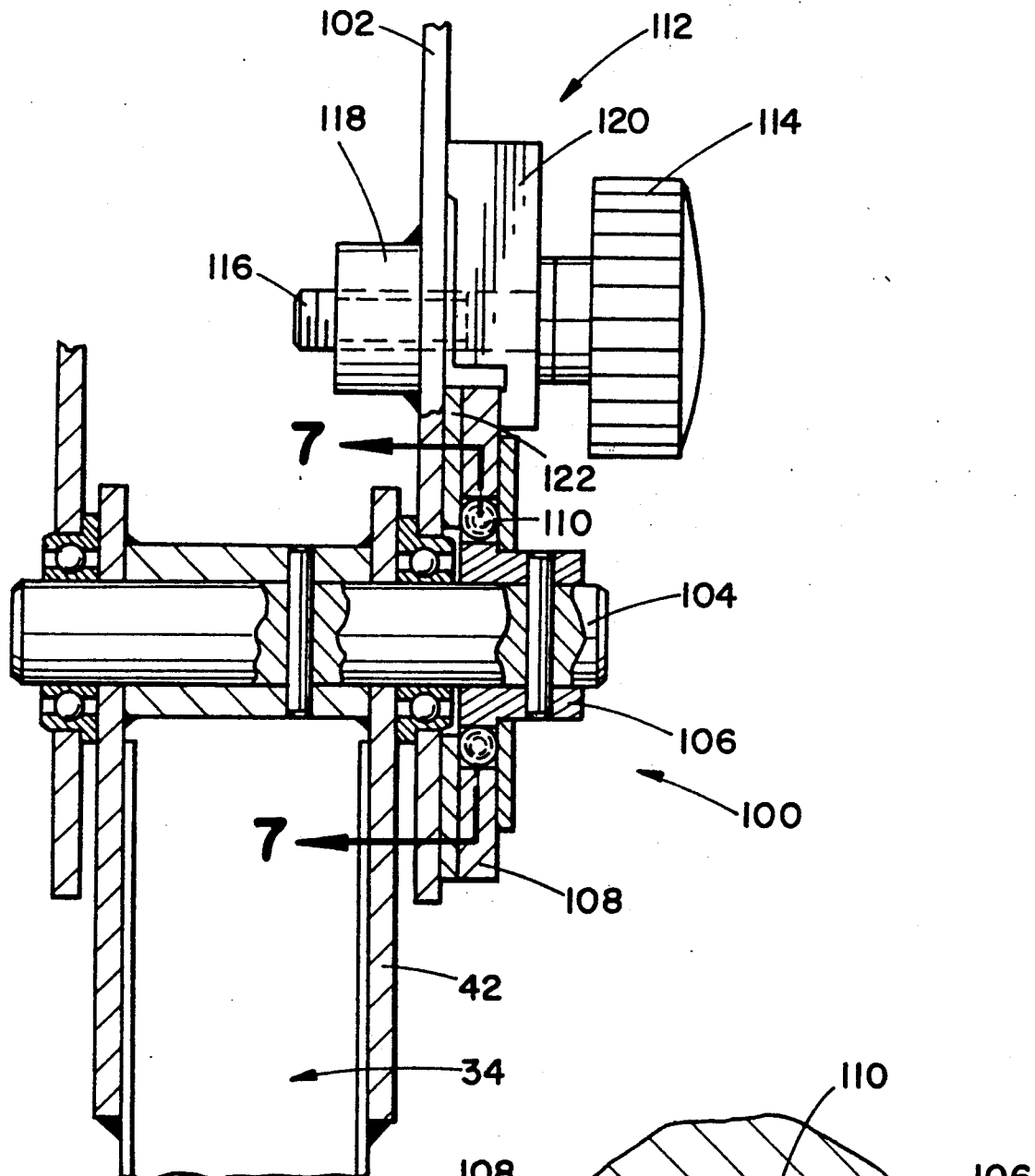
FIG. 6 is a cross-sectional view taken generally along the lines 6—6 of FIG. 5.
Figure 7:
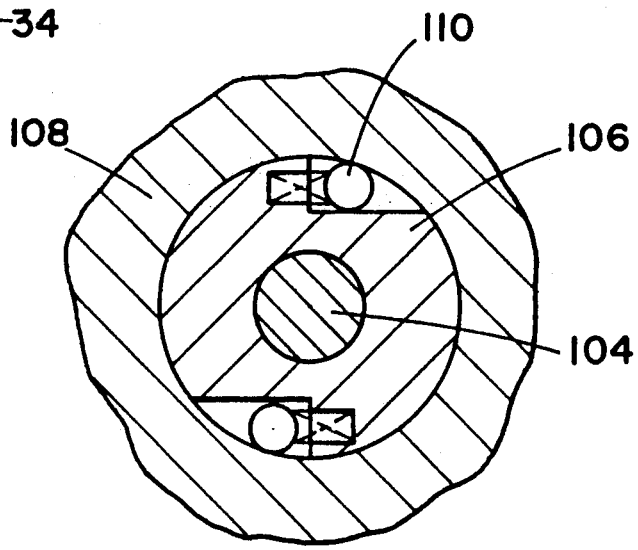
FIG. 7 is a cross-sectional view taken generally along the lines 7—7 of FIG. 6.

Since the x-ray source is always urged toward the first, upper location, an operator or diagnostician must be able to lock the source in place at a lower intermediate position. To accomplish this, and as further shown in FIGS. 5–7 a clutch means 100 is associated with either the mounting member or base member. In the preferred arrangement, the clutch means is defined at the interconnection of the arm 34 with the mounting member. The second end 42 of the arm is connected to a flange 102 of the mounting member through the clutch means. Second end 42 is non-rotatably secured to pin 104 which is non-rotatably secured to inner race 106. An outer race 108 is disposed about the inner race and rotates in only one direction with respect to the inner race depending on the direction of rotation of the inner race. As more particularly illustrated in FIG. 7, if the inner race rotates in a clockwise direction, the outer race overrides the inner race, thus permitting free rotation therebetween. On the other hand, if the inner race is rotated in a counterclockwise direction, the outer race is engaged by clutch rollers 110 and rotates therewith in a manner well known in the art. The flange 102, on the other hand, is selectively secured to outer raCe 108.

The outer race and the flange are selectively clamped together by a locking means 112. The locking means includes a handle 114 having a threaded member 116 extending through the flange 102 to cooperate With a nut 118. A pressure plate 120 and disk 122 are received between the handle and flange 102 on opposite sides of the outer race so that rotation of the threaded member in one direction advances the pressure plate into clamping engagement with the outer race. That is, the outer race 108, disk 122 and flange 102 are clamped together to inhibit rotation. The clutch means can be deactuated by rotating the handle in the opposite direction and removing the force acting on pressure plate 120 from the flange so that the flange is free to rotate relative to the arm 34 in either direction. In the latter situation, the biasing force of the fluid cylinder will then urge the mounting member and source to the upper location. If, though, the pressure plate is actuated by the locking means, upward movement of the arm around pivot pin 90 is prohibited because of the clutch assembly. Further, downward or counterclockwise rotation of the arms 32, 34, though, is permitted so that an operator can continue to move the source downward if desired.

A chief benefit of this arrangement is that the restricted orifice so in the piston will only allow a predetermined amount of fluid to be passed between the first and second chambers. Thus, the piston will move slowly with controlled velocity in either direction. Additionally, if a leak occurs around the piston, that is if the fluid cylinder fails, the x-ray source will still have a tendency to move in a much slower fashion to the storage position as shown by B" in FIG. 1 above the platform 22. Thus, the one way clutch 100 insures that the source cannot be locked in its upper position without sufficient gas pressure in the cylinder to hold it there.

To summarize, the x-ray source can always be moved in a counterclockwise direction from its first upper location B toward the storage position B". If the clutch is deactuated, the predetermined differential areas on the piston, as well as the predetermined cylinder pressure, exert a biasing force on the first arm that urges the x-ray source toward the first, upper location. On the other hand, if the clutch means is actuated, rotation of the arms 32, 34 in a clockwise manner is prohibited while continued counterclockwise or downward movement of the x-ray source is permitted.

Figure 8:
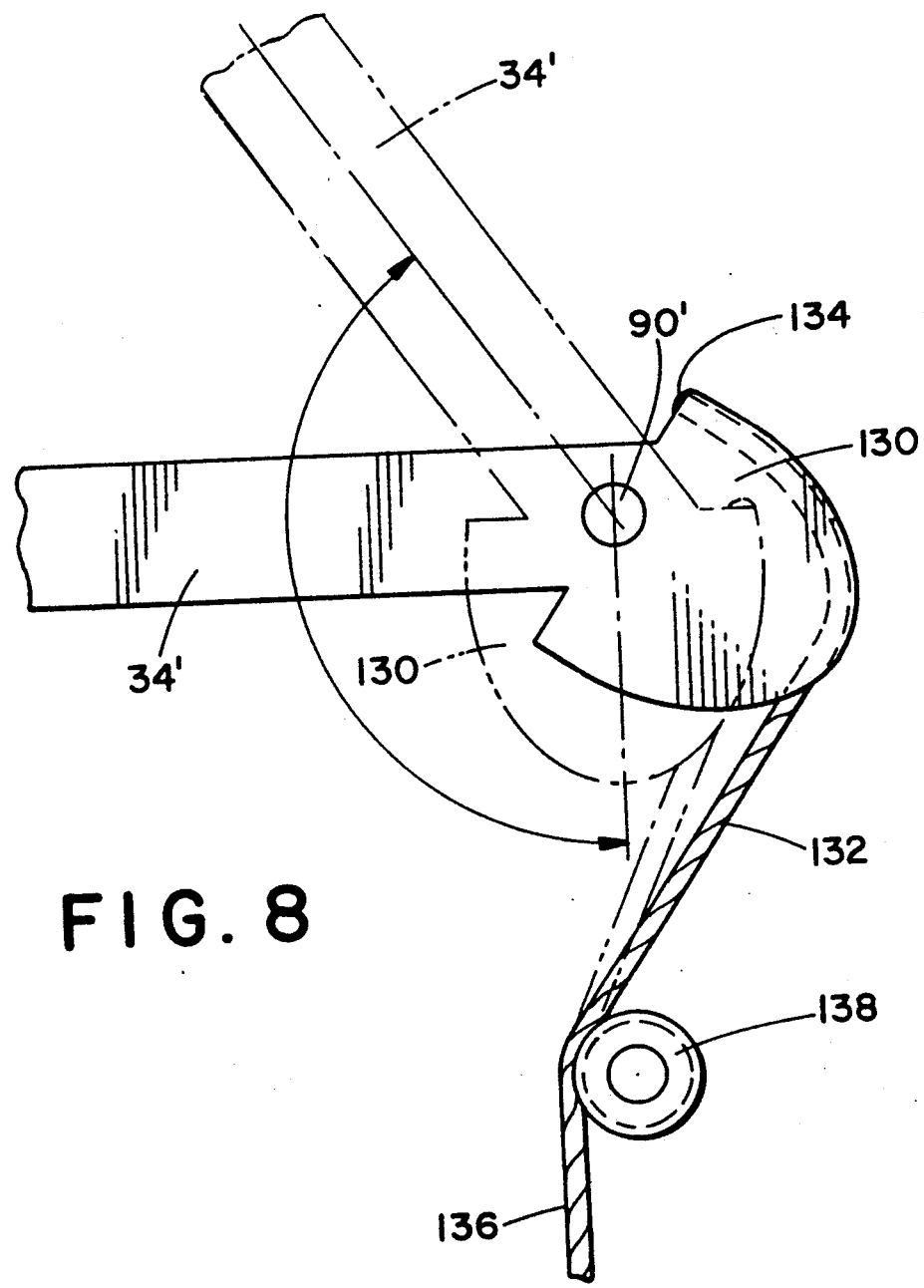
FIG. 8 is an elevational view of an alternative interconnection between the arm and fluid biasing member.

Turning now to FIG. 8, like numerals with a primed suffix (') will refer to like elements, while new numerals will refer to new elements. Specifically, arm 34' is secured to an eccentric cam 130 in place of the link arm used in the previously described embodiment. A cable 132 has one end 134 attached to the cam and a second end 136 attached to the end of the rod (not shown). Disposed between the cam and the rod is an idler pulley 138 that orients the cable for connection with the fluid biasing means.

The use of the eccentric cam adjusts the amount of the biasing force as the arm rotates about the pin 90'. Thus, as the arm becomes horizontal, the cable must undergo maximum travel about the eccentric cam as illustrated in FIG. 8. Of course still other arrangements directed to adjusting the amount of biasing force as the arm rotates can be used without departing from the scope and intent of the invention.

An alternative fluid biasing means is illustrated in FIG. 9. The gas cylinder assembly 52 is retained but is supplemented through the addition of a cylinder assembly 152 that uses a liquid, such as oil, rather than gas as used in the cylinder assembly 52. Preferably the cylinder assembly 152 operates in parallel with the above described gas cylinder assembly. The additional cylinder assembly has substantially the same structural components as the gas cylinder assembly, i.e., cylinder 154, piston 156 defining first and second chambers 158, 160, and a rod 162 that is operatively associated with the arm 34. An orifice 180 is also provided in the piston to control movement of the piston, and hence the arm 34.

The addition of the liquid cylinder assembly provides a dashpot type arrangement used in conjunction with the air cylinder assembly. The air cylinders serve solely as energy storage devices, while the liquid cylinder controls the rate at which the energy can be released. This parallel arrangement greatly enhances the velocity control required for operation of the counterbalance assembly since liquid flow through the orifice 180 is a more responsive control than gas through an orifice.

FIG. 10 shows a "dead man" control that may also be incorporated into the counterbalance assembly to provide a second clutch means for controlling movement of the x-ray source. More particularly, a cable 170 is secured at one end 172 to the base member C. The cable is then wrapped in a clockwise direction around the pin 90, preferably a few times, and a second end 174 secured along the arm 34. An actuating button 176 is biased outwardly by a spring 178 that cooperates with a shoulder 182. Upon depression of the button, the cable is slackened and the gripping action otherwise imposed about the pin is released. This permits the arms and x-ray source to move upwardly, assuming the clutch means is not actuated. On the other hand, the source can be moved downwardly without depressing the button 176 because of the wrapping direction of the cable around the pin 90. Of course other suitable deadman arrangements may be used within the scope and intent of this invention.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A counterbalance assembly for supporting diagnostic imaging equipment, the assembly comprising:
   a base member;
   a first arm having a first end pivotally secured to the base member for selective movement relative thereto;
   a mounting member secured to a second end of the first arm;
   fluid biasing means operatively associated with the first arm for urging the mounting member toward a first location; and
   a clutch means for selectively controlling movement and permitting one-way movement between the mounting member and the base member.

2. The counterbalance assembly as set forth in claim 1 further comprising locking means for selectively actuating the clutch means.

3. The counterbalance assembly as set forth in claim 1 further comprising locking means for actuating the clutch means to permit selective one-way and two-way pivoting between the first arm and the mounting member.

4. The counterbalance assembly as set forth in claim 1 further comprising a bent link arm interposed between the first arm and the fluid biasing means.

5. The counterbalance assembly as set forth in claim 1 further comprising an eccentric cam interposed between the first arm and the fluid biasing means.

6. The counterbalance assembly as set forth in claim 5 further comprising a cable having a first end operatively associated with the cam and a second end operatively associated with the fluid biasing means.

7. The counterbalance assembly as set forth in claim 1 wherein the fluid biasing means includes a gas cylinder assembly having a cylinder receiving a piston therein for dividing the cylinder into first and second chambers, and a rod extending from one face of the piston and from the cylinder, the rod being operatively connected to the first arm.

8. The counterbalance assembly as set forth in claim 7 wherein the piston includes an orifice extending therethrough for establishing communication between the first and second chambers.

9. A counterbalance assembly for supporting diagnostic imaging equipment, the assembly comprising:
   a base member;
   a mounting member adapted to receive diagnostic imaging equipment;
   first and second arms interposed between the base member and the mounting member for varying the dimension between the base member and mounting member and maintaining a parallel relationship therebetween;
   fluid biasing means operatively associated with the first arm for urging the mounting member toward a first location;
   a clutch means interposed between the mounting member and the base member for inhibiting movement of the mounting member toward the first location; and
   locking means for selectively actuating the clutch means.

10. The counterbalance assembly as set forth in claim 9 wherein the fluid biasing means includes a gas cylinder assembly having a cylinder receiving a piston therein dividing the cylinder into first and second chambers, a rod extending outwardly from one face of the piston and through the cylinder for operative connection with the first arm, and a passage defined through the piston for establishing communication between the first and second chambers.

11. A counterbalance assembly adapted to support diagnostic imaging equipment, the assembly comprising:
   a base member;
   a mounting member adapted to receive diagnostic imaging equipment;
   first and second arms interconnecting the base member and the mounting member, each arm having a first end pivotably secured to the base member and each arm having a second end pivotally secured to the mounting member;
   clutch means associated with the first arm for limiting movement between the first arm and the mounting members; and
   fluid biasing means operatively associated with one of the first and second arms for urging the mounting member toward a first location.

12. The counterbalance assembly as set forth in claim 11 wherein the clutch means will permit the mounting member to move to a storage position if the fluid biasing means fails.

13. The counterbalance assembly as set forth in claim 11 further comprising a locking means for selectively actuating the clutch means to permit (i) one-way pivotal movement and (ii) two-way pivotal movement between the first arm and the mounting member.

14. The counterbalance assembly as set forth in claim 11 further comprising a bent link having a first end engaging the first arm and a second end engaging the fluid biasing means.

15. The counterbalance assembly as set forth in claim 11 further comprising an eccentric cam interposed between the first arm and the fluid biasing means for adjusting the amount of biasing force in accordance with the location of the first arm.

16. The counterbalance assembly as set forth in claim 15 further comprising a cable having a first end secured to the first arm through the eccentric cam and a second end secured to the fluid biasing means.

17. The counterbalance assembly as set forth in claim 12 wherein the fluid biasing means includes a gas cylinder assembly and a liquid cylinder assembly operating in parallel relation to control the velocity of the mounting member.

18. The counterbalance assembly as set forth in claim 12 further comprising a second clutch means associated with the first arm for limiting movement between the first arm and the mounting member.

19. In a portable diagnostic imaging assembly including a base member, a mounting member adapted to receive a non-invasive examination means, a four-bar linkage operatively interconnecting the base member and mounting member, and a counterbalance assembly for urging the mounting member toward and upper location, the counterbalance assembly including a fluid biasing means operatively associated with the four bar linkage and a clutch means for selectively inhibiting movement of the mounting member and associated non-examination means toward the upper location and permitting movement of the mounting member toward a lower storage position.

20. The portable diagnostic imaging assembly as defined in claim 19 further comprising locking means for selectively actuating the clutch means to alternatively permit one-way and two-way pivoting between the mounting member and base member.

21. The portable diagnostic imaging assembly as defined in claim 20 wherein the fluid biasing means includes a gas cylinder assembly having a cylinder divided into first and second chambers by a piston received therein, a rod extending outwardly from one face of the piston and through the cylinder for operative connection with the four bar linkage, and a passage defined through the piston for establishing communication between the first and second chambers.

22. The portable diagnostic imaging assembly as defined in claim 19 further comprising an eccentric cam interposed between the four bar linkage and the fluid biasing means for adjusting the amount of biasing force in accordance with the location of the four bar linkage.

23. The portable diagnostic imaging assembly as defined in claim 19 wherein the fluid biasing means includes a gas cylinder assembly and a liquid cylinder assembly operating in parallel relation to control the velocity of the mounting member.

* * * * *